United States Patent [19]

Rossignol

[11] Patent Number: 4,521,424
[45] Date of Patent: Jun. 4, 1985

[54] QUINATE SALTS OF THE ANTIMALARIAL COMPOUND MEFLOQUINE

[75] Inventor: Jean F. Rossignol, Philadelphia, Pa.

[73] Assignee: SmithKline Beckman Corporation, Philadelphia, Pa.

[21] Appl. No.: 584,183

[22] Filed: Feb. 27, 1984

[51] Int. Cl.³ .................... C07D 401/06; A61K 31/47
[52] U.S. Cl. .................................. 514/314; 546/176
[58] Field of Search .......................... 548/176; 424/258

[56] References Cited

U.S. PATENT DOCUMENTS 4,284,627  8/1981  Raether et al. ..................... 424/229

OTHER PUBLICATIONS

Am. J. Trop. Med. Hyg., 32(3), 1983, pp. 447–451.
Ohnmacht et al., J. Med. Chem., vol. 14, No. 10, pp. 926–928, (1971).

*Primary Examiner*—Glennon H. Hollrah
*Assistant Examiner*—D. B. Springer

*Attorney, Agent, or Firm*—Richard D. Foggio; Alan D. Lourie

[57] ABSTRACT

The compound of formula (I)

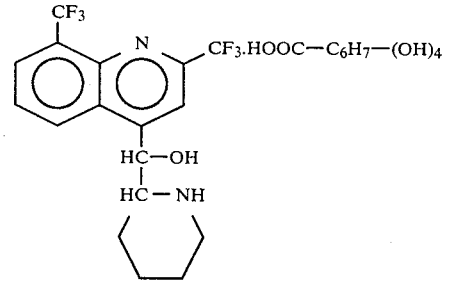

possesses markedly increased solubility under aqueous conditions and improved pharmacokinetic profile against malaria-causing parasites. Pharmaceutical compositions and method of treatment of subjects with malaria are also disclosed.

6 Claims, No Drawings

QUINATE SALTS OF THE ANTIMALARIAL COMPOUND MEFLOQUINE

BACKGROUND OF THE INVENTION

Mefloquine, α-2-piperidinyl-2,8-bis(trifluoromethyl)-4-quinolinemethanol, has been shown to exhibit antimalarial activity in humans against both chloroquine-sensitive and resistant strains of Plasmodium falciparum.

SUMMARY OF THE INVENTION

This invention relates to the quinate salt of α-2-piperidinyl-2,8-bis(trifluoromethyl)-4-quinolinemethanol. This salt exhibits markedly increased solubility under aqueous conditions and improved pharmacokinetic profile against malaria-causing parasites when compared to the hydrochloride salt reported in the literature. Pharmaceutical compositions and methods of treatment of subjects with malaria are also disclosed.

DETAILED DESCRIPTION OF THE INVENTION

The compound represented by the following structural formula (I):

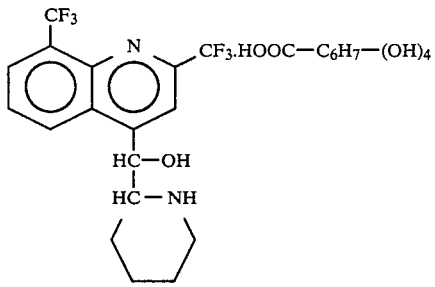

possesses improved pharmacokinetic profile against malaria-causing parasites. The compound of the formula (I), Mefloquine quinate, is unexpectedly soluble in water in view of the relative insolubility of Mefloquine hydrochloride in water. In comparison tests, the solubility of Mefloquine quinate was shown to be 100 g/100 ml of water and the solubility of Mefloquine hydrochloride was 1 g/100 ml of water.

The compound of this invention is conveniently prepared by reacting quinic acid (1,3,4,5-tetrahydroxycyclohexanecarboxylic acid) with Mefloquine (free base) (II):

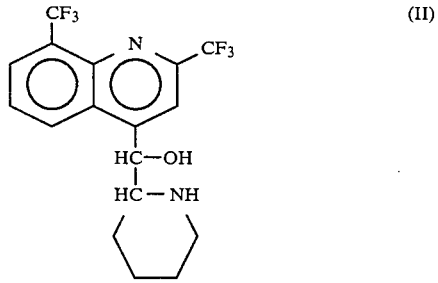

in an inert solvent. The amount of quinic acid employed in this reaction can be between 0.75 and 1.50 moles per mole of Mefloquine (II) but 1.0 moles of quinic acid is preferred. Mefloquine (II) is mixed with the appropriate amount of quinic acid (50% aqueous solution) and the inert solvent is added to affect solution of the reactants at a temperature selected from the range of ambient temperature to 100° C. The reaction solution is filtered and the filtrate is heated under reduced pressure up to 100° C. to remove the solvent. Upon concentration to dryness, the compound of the formula (I) solidifies and is collected and dried.

Examples of the inert solvents which are utilized in the process are alcohols, such as, methanol, ethanol, isopropanol and the like and amides, such as dimethylformamide and dimethylacetamide.

Mefloquine (II) is a known compound and prepared according to general procedures.

The antimalarial activity of the compound of this invention is demonstrated in standard pharmacological in vitro test procedures against P. falciparum.

The antimalarial activity of α-2-piperidinyl-2,8-bis(trifluoromethyl)-4-quinolinemethanol quinate (Mefloquine quinate) was established utilizing the procedure described by Lebras et al. in the American Journal of Tropical Medicine and Hygiene, Vol. 32 (3) pages 447–451 (1983). Mefloquine quinate was compared with Mefloquine hydrochloride against two strains of P. falciparum from human isolates. The results of the Lebras procedure expressed as an $IC_{50}$ (inhibitory concentration was calculated from the simple graph of the percentage of maturation of the schizonts against the log concentration of the test drug) are shown below:

| | $IC_{50}$ (mM/l) | |
|---|---|---|
| Strain | Mefloquine quinate | Mefloquine hydrochloride |
| FCM 17 Strains West African Chloroquine-sensitive | 175 (116.1)* | 120 (109.4)* |
| FCM 24 Strains Guyanne Chloroquine-resistant | 140 (92.9)* | 120 (109.4)* |

*The figures in parentheses are $IC_{50}$ based on Mefloquine (free base).

Mefloquine quinate has demonstrated comparable efficacy with Mefloquine hydrochloride in this standard in vitro test procedure. Since, however, the aqueous solubility of Mefloquine quinate is so surprisingly greater than that of Mefloquine hydrochloride, its pharmacokinetic profile would be improved.

The pharmaceutical compositions of this invention containing the compound of formula (I) which has antimalarial activity are prepared in conventional dosage unit forms by incorporating the chemical compound with a nontoxic pharmaceutical carrier according to accepted procedures. A nontoxic quantity of said active ingredient is chosen which is sufficient to produce the desired chemotherapeutic activity in a subject, animal or human, without unacceptable toxicity. The compositions will contain the active ingredient in such an effective but nontoxic amount selected from about 125 mg to about 1000 mg of active ingredient per dosage unit but this quantity depends on the specific biological activity desired, the activity of the compound and the conditions of the patient.

A wide variety of pharmaceutical forms can be employed. Thus, if a solid carrier for oral administration is used the preparation can be tableted, placed in a hard gelatin capsule in powder or pellet form, or in the form of a suppository, trouche or lozenge. The amount of solid carrier will vary widely but preferably will be from about 125 mg to about 500 mg. If a liquid carrier is used, the preparation will be in the form of a syrup, emulsion, soft gelatin capsule, sterile injectable liquid such as an ampul, or an aqueous solution or nonaqueous liquid suspension. In view of the solubility of the compound of formula (I), aqueous solutions are readily prepared and utilized as a sterile injectable liquid formulation.

The pharmaceutical preparations are made following the conventional technique of the pharmaceutical chemist involving mixing, granulating and compressing when necessary, or variously mixing and dissolving the ingredients as appropriate to give the desired end product.

The method of producing antimalarial activity, curatively or prophylactically, comprises administering internally to a subject in need of such activity a compound of formula (I), usually combined with a pharmaceutical carrier, in a nontoxic amount sufficient to produce said activity as described above. The route of administration may be any route which effectively transports the active compound to the site of action which is to be affected within the body such as orally or parenterally. Advantageously, a single oral dose or equal oral doses will be administered several times such as from 1–3 times a day with the daily dosage regimen being selected from about 125 mg to about 1000 mg. Alternatively, a single parenteral dose will be administered once a day with a daily dosage regimen equivalent to that of the oral formulation.

The following examples illustrate the preparations of the compound of formula (I) and its incorporation into pharmaceutical compositions and as such are not to be considered as limiting the invention set forth in the claims appended hereto.

EXAMPLE 1

Preparation of α-2-piperidinyl-2,8-bis(trifluoromethyl)-4-quinolinemethanol quinate (Compound A)

To a 50% aqueous solution of quinic acid (1.9 g) at ambient temperature with stirring was added α-2-piperidinyl-2,8-bis(trifluoromethyl)-4-quinolinemethanol (1 g). To the mixture was added ethanol (10 ml) and the mixture was heated to about 40° C. to affect solution. The solution was then filtered and the ethanol and water removed under vacuum until dryness. The desired product solidified as a white crystalline material with a melting point of 180° C. and was soluble in water. Elemental analysis is as follows: Calculated C, 50.49; H, 4.90; N, 4.90 and F, 19.81. Found C, 50.61; H, 4.71; N, 4.72 and F, 19.86.

EXAMPLE 2

As a specific embodiment of a composition of this invention, an active ingredient, such as one part of Compound A, is dissolved in 20 parts water and is administered orally in one dose of 4 mg/kg to a subject in need of treatment of malaria.

What is claimed is:

1. A compound represented by the following structural formula (I):

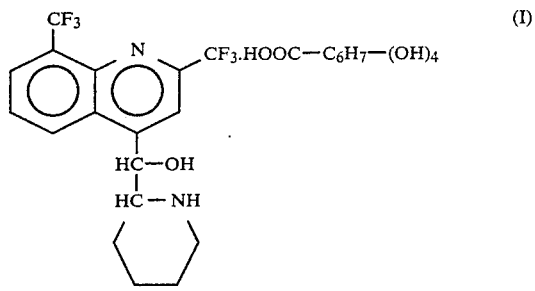

which is α-2-piperidinyl-2,8-bis(trifluoromethyl)-4-quinolinemethanol quinate.

2. A pharmaceutical composition for the treatment of malaria comprising a nontoxic antimalarial quantity of a compound of claim 1 and a pharmaceutically acceptable carrier therefor.

3. A composition of claim 2 in a form suitable for parenteral administration.

4. A composition of claim 3 in the form of a sterile aqueous solution.

5. A composition of claim 2 in which the quantity of the compound is selected from the range of from 125 mg. to about 1000 mg.

6. A method for the treatment of malaria in a subject in need of said treatment comprising administering orally or by injection a nontoxic antimalarial quantity of a compound of claim 1.

* * * * *